(12) United States Patent
Hardy et al.

(10) Patent No.: US 11,678,884 B2
(45) Date of Patent: *Jun. 20, 2023

(54) CLOSING DEVICE FOR TISSUE OPENINGS

(71) Applicant: Muffin Incorporated, West Lafayette, IN (US)

(72) Inventors: Gregory James Hardy, Winston Salem, NC (US); Shaun Davis Gittard, Winston Salem, NC (US); John C. Sigmon, Jr., Winston-Salem, NC (US); William J. Havel, West Lafayette, IN (US); Jeremy T. Newkirk, West Lafayette, IN (US); Neal E. Fearnot, West Lafayette, IN (US); Rita Hadley, Otterbein, IN (US)

(73) Assignee: Muffin Incorporated, West Lafayette, IN (US)

( * ) Notice: Subject to any disclaimer, the term of this patent is extended or adjusted under 35 U.S.C. 154(b) by 465 days.

This patent is subject to a terminal disclaimer.

(21) Appl. No.: 16/796,311

(22) Filed: Feb. 20, 2020

(65) Prior Publication Data

US 2020/0178963 A1 Jun. 11, 2020

Related U.S. Application Data

(63) Continuation of application No. 15/602,457, filed on May 23, 2017, now Pat. No. 10,568,628.

(51) Int. Cl.
*A61B 17/08* (2006.01)
*A61B 17/10* (2006.01)
(Continued)

(52) U.S. Cl.
CPC .......... *A61B 17/08* (2013.01); *A61B 17/0057* (2013.01); *A61B 17/10* (2013.01); *A61B 17/12122* (2013.01); *A61B 17/12145* (2013.01); *A61B 2017/00575* (2013.01); *A61B 2017/00592* (2013.01); *A61B 2017/00597* (2013.01);
(Continued)

(58) Field of Classification Search
None
See application file for complete search history.

(56) References Cited

U.S. PATENT DOCUMENTS 3,416,534 A 12/1968 Quinn
4,368,730 A 1/1983 Sharrock
(Continued)

FOREIGN PATENT DOCUMENTS

EP 1 275 351 8/2004
JP 2011-076403 2/1999
(Continued)

OTHER PUBLICATIONS

Communication pursuant to Rules 161(1) and 162 EPC for European Patent Applicatoin No. 15734001.9 dated Feb. 15, 2017, 2 pgs.
(Continued)

*Primary Examiner* — Shaun L David
(74) *Attorney, Agent, or Firm* — Woodard Emhardt Henry Reeves & Wagner LLP

(57) ABSTRACT

There are shown and described embodiments of a closure device for closing holes in tissue, for example in the right atrial appendage. The closure device in particular embodiments includes first and second mesh closure members and a tether or stem connecting them. Embodiments of a delivery device for the closure device are also described.

20 Claims, 6 Drawing Sheets

(51) Int. Cl.
*A61B 17/00* (2006.01)
*A61B 17/12* (2006.01)
*A61B 90/00* (2016.01)

(52) U.S. Cl.
CPC ............... *A61B 2017/00606* (2013.01); *A61B 2017/00619* (2013.01); *A61B 2017/00623* (2013.01); *A61B 2017/081* (2013.01); *A61B 2017/1205* (2013.01); *A61B 2090/3966* (2016.02)

(56) References Cited

U.S. PATENT DOCUMENTS

| | | | |
|---|---|---|---|
| 4,907,598 | A | 3/1990 | Bauer |
| 5,059,193 | A | 10/1991 | Kuslich |
| 5,081,997 | A | 1/1992 | Bosley, Jr. et al. |
| 5,116,357 | A | 5/1992 | Eberbach |
| 5,122,155 | A | 6/1992 | Eberbach |
| 5,228,451 | A | 7/1993 | Bales et al. |
| 5,258,000 | A | 11/1993 | Gianturco |
| 5,308,324 | A | 5/1994 | Hammerslag et al. |
| 5,312,435 | A | 5/1994 | Nash et al. |
| 5,366,460 | A | 11/1994 | Eberbach |
| 5,372,587 | A | 12/1994 | Hammerslag et al. |
| 5,397,331 | A | 3/1995 | Himpern et al. |
| 5,545,178 | A | 8/1996 | Kensey et al. |
| 5,549,633 | A | 8/1996 | Evans et al. |
| 5,607,407 | A | 3/1997 | Tolkoff et al. |
| 5,662,681 | A | 9/1997 | Nash et al. |
| 5,683,411 | A | 11/1997 | Kavteladze et al. |
| 5,700,277 | A | 12/1997 | Nash et al. |
| 5,728,114 | A | 3/1998 | Evans et al. |
| 5,733,294 | A | 3/1998 | Forber et al. |
| 5,743,891 | A | 4/1998 | Tolkoff et al. |
| 5,846,261 | A | 12/1998 | Kotula et al. |
| 5,906,594 | A | 5/1999 | Scarfone et al. |
| 5,944,738 | A | 8/1999 | Amplatz et al. |
| 6,123,715 | A | 9/2000 | Amplatz |
| 6,126,633 | A | 10/2000 | Kaji et al. |
| 6,210,377 | B1 | 4/2001 | Ouchi |
| 6,456,874 | B1 | 9/2002 | Hafer et al. |
| 6,689,122 | B2 | 2/2004 | Yamamoto |
| 7,488,347 | B1 | 2/2009 | Goble et al. |
| 7,897,167 | B2 | 3/2011 | Armstrong et al. |
| 8,277,481 | B2 | 10/2012 | Kawaura et al. |
| 2003/0004579 | A1 | 1/2003 | Rousseau et al. |
| 2003/0088256 | A1 | 5/2003 | Conston et al. |
| 2004/0049231 | A1 | 3/2004 | Hafer et al. |
| 2005/0070948 | A1 | 3/2005 | Kirsteins |
| 2006/0052816 | A1 | 3/2006 | Bates et al. |
| 2006/0241690 | A1 | 10/2006 | Amplatz et al. |
| 2006/0247680 | A1 | 11/2006 | Amplatz et al. |
| 2007/0225760 | A1 | 9/2007 | Moszuer et al. |
| 2007/0233186 | A1 | 10/2007 | Meng |
| 2007/0265658 | A1 | 11/2007 | Nelson et al. |
| 2007/0282430 | A1 | 12/2007 | Thommen et al. |
| 2008/0033478 | A1 | 2/2008 | Meng |
| 2008/0071301 | A1 | 3/2008 | Matsuura et al. |
| 2008/0119886 | A1 | 5/2008 | Greenhalgh et al. |
| 2009/0062844 | A1 | 3/2009 | Tekulve et al. |
| 2009/0082803 | A1 | 3/2009 | Adams et al. |
| 2009/0099647 | A1 | 4/2009 | Glimsdale et al. |
| 2009/0204130 | A1 | 8/2009 | Kantsevoy et al. |
| 2009/0204133 | A1 | 8/2009 | Melzer et al. |
| 2009/0275974 | A1 | 11/2009 | Marchand et al. |
| 2009/0281557 | A1 | 11/2009 | Sander et al. |
| 2009/0287229 | A1 | 11/2009 | Ogdahl |
| 2009/0306706 | A1 | 12/2009 | Osypka |
| 2010/0030256 | A1 | 2/2010 | Dubrual et al. |
| 2010/0211046 | A1 | 8/2010 | Adams et al. |
| 2011/0152993 | A1 | 6/2011 | Marchand et al. |
| 2012/0016409 | A1 | 1/2012 | Sherwinter et al. |
| 2014/0018841 | A1 | 1/2014 | Peiffer et al. |
| 2014/0257360 | A1 | 9/2014 | Keillor |
| 2014/0257361 | A1 | 9/2014 | Prom |
| 2014/0277119 | A1 | 9/2014 | Akpinar |
| 2014/0343602 | A1 | 11/2014 | Cox et al. |
| 2015/0032153 | A1 | 1/2015 | Quadri et al. |
| 2015/0257763 | A1 | 9/2015 | Blum et al. |
| 2015/0374475 | A1 | 12/2015 | McLawhorn et al. |
| 2016/0249935 | A1 | 9/2016 | Hewitt et al. |
| 2017/0014114 | A1 | 1/2017 | Rafiee et al. |
| 2017/0156904 | A1 | 6/2017 | Liu et al. |
| 2018/0132856 | A1 | 5/2018 | Wierzbicki et al. |
| 2018/0280006 | A1 | 10/2018 | Rogers et al. |
| 2019/0183481 | A1 | 6/2019 | Rohl et al. |

FOREIGN PATENT DOCUMENTS

| | | |
|---|---|---|
| WO | WO 2005/092203 A1 | 10/2005 |
| WO | WO 2005/110240 A1 | 11/2005 |
| WO | WO 2006/119034 B2 | 11/2006 |
| WO | WO 2008/019590 A1 | 2/2008 |
| WO | WO 2013/028579 A1 | 2/2013 |

OTHER PUBLICATIONS

International Application No. PCT/US2018/034112 International Search Report and Written Opinion, dated Nov. 2, 2018, 14pgs.
International Search Report and Written Opinion for PCT/2011/034285 dated Jul. 8, 2011, 12 pgs.
International Search Report and Written Opinion for PCT/US2015/037378, dated Aug. 7, 2015, 12 pgs.
Response to Communication pursuant to Rules 161(1) and 162 EPC for European Patent Application No. 15734001.9 filed Aug. 23, 2017, 9 pgs.

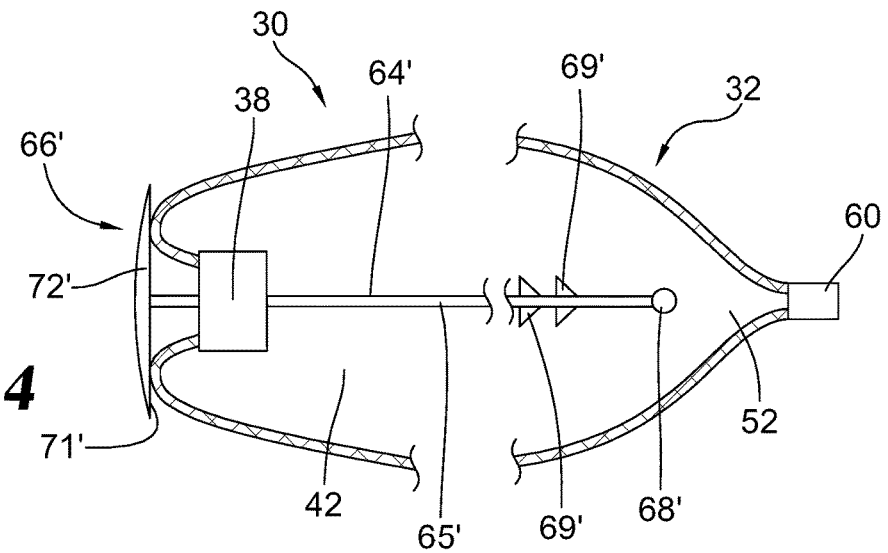
*Fig. 4*
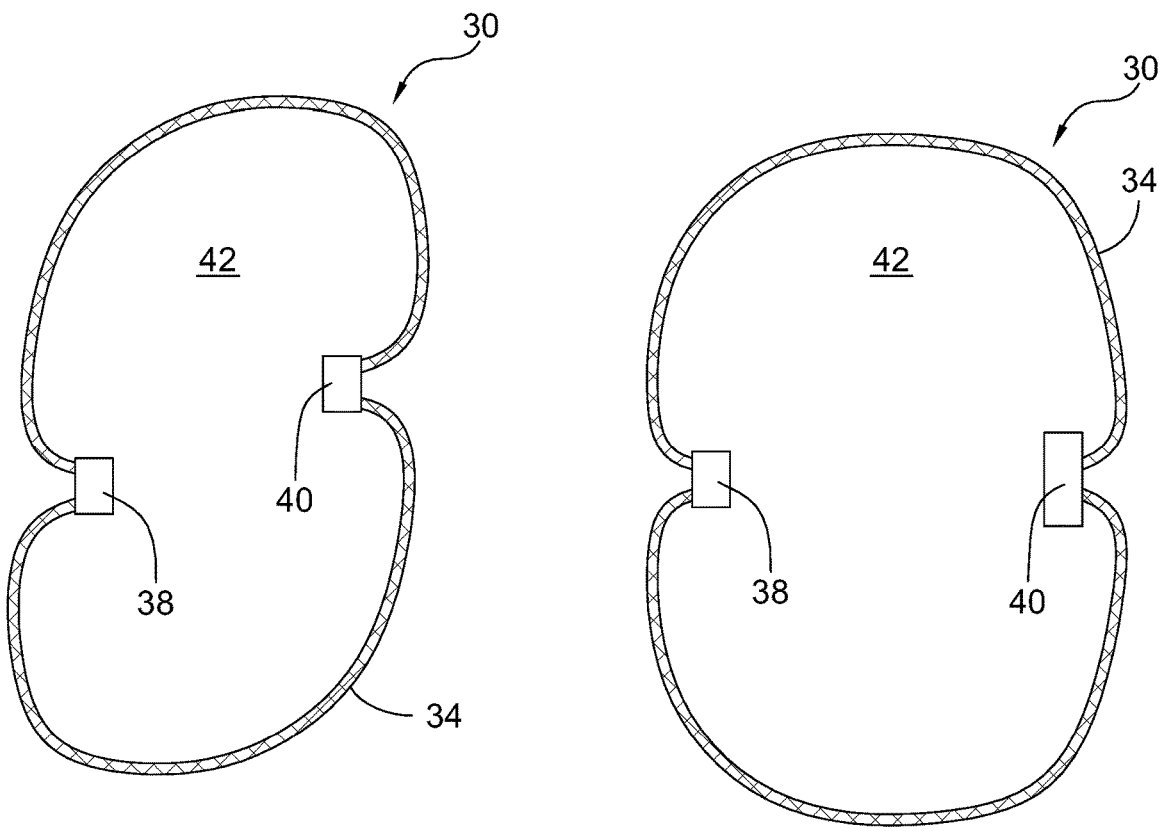
*Fig. 5*
*Fig. 6*

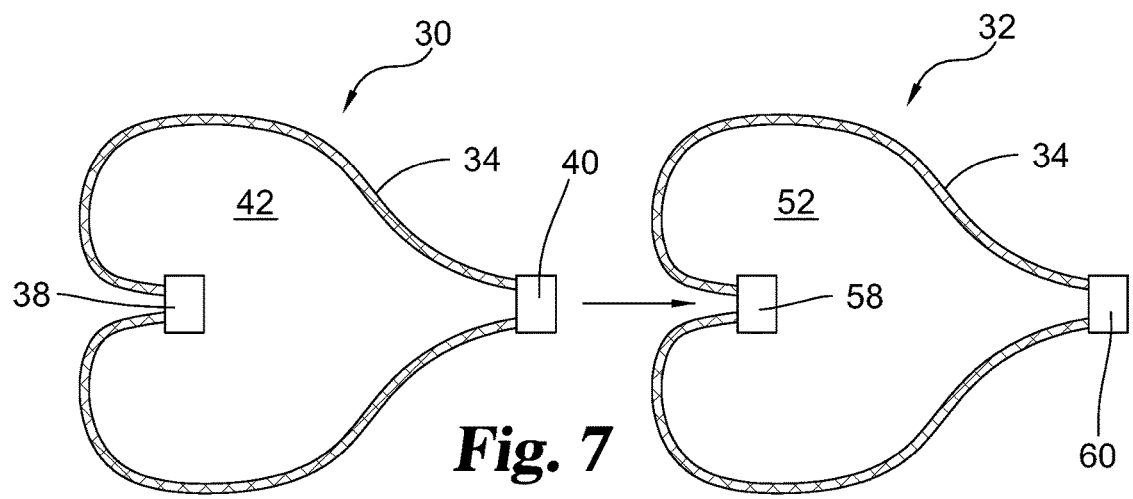
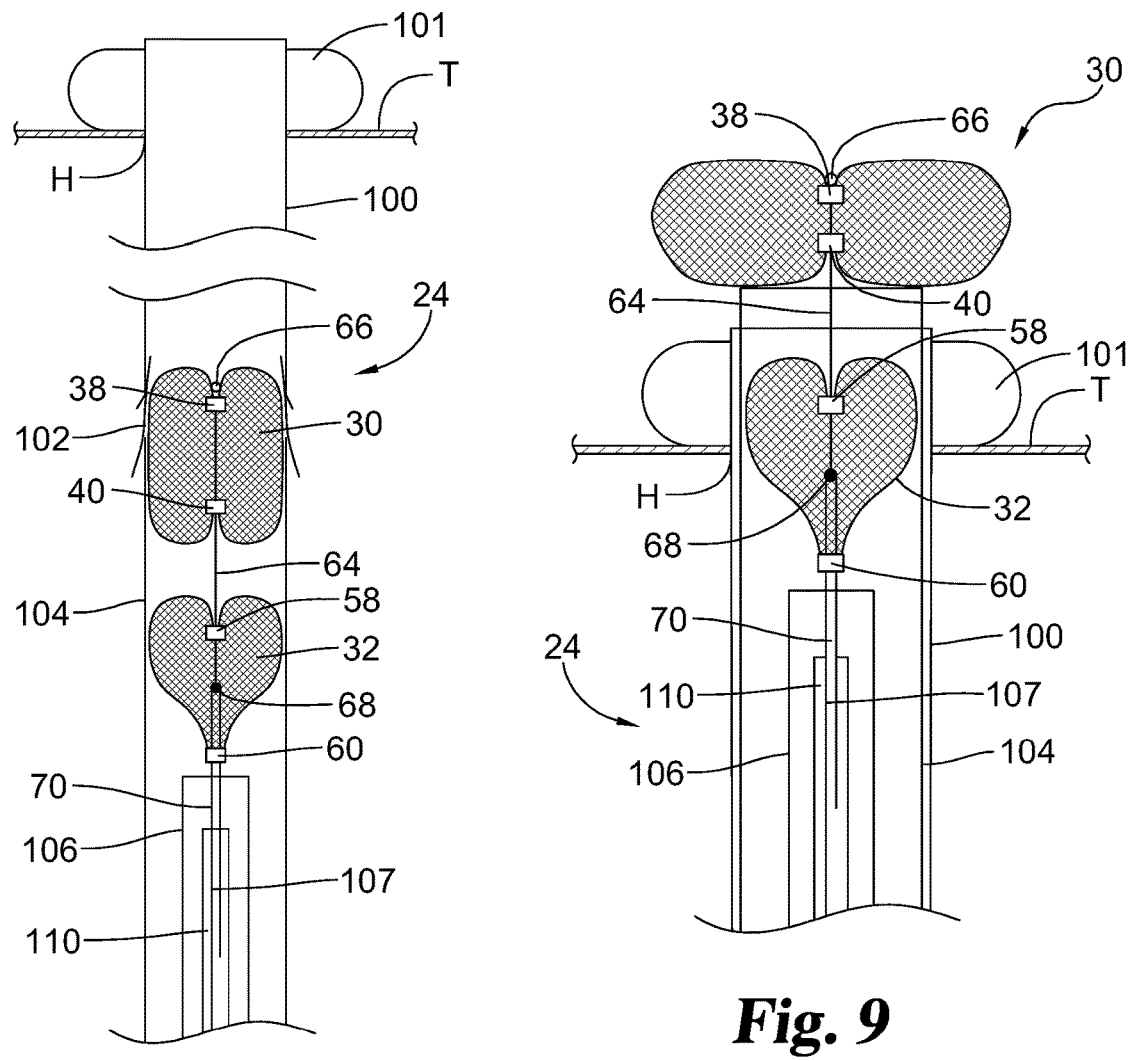

CLOSING DEVICE FOR TISSUE OPENINGS

This application is a continuation of application Ser. No. 15/602,457, filed on May 23, 2017, which is incorporated by reference in its entirety.

The present application discloses structure and methods for closing internal tissue openings in a minimally-invasive manner. More specifically, a closure with two connected mesh structures is disclosed that may be used to close a minimally-invasive surgical opening in the heart or other organ.

BACKGROUND

Minimally-invasive surgical procedures have been developed for many treatments, including placement of medical devices inside a patient or other therapeutic or diagnostic purposes, as a way of reducing trauma to a patient. In such procedures, holes are made and accessed by catheters or similar devices, and treatment devices are passed through the catheters to the site of interest. When the procedure or a part of it is concluded, the access catheter is removed and the hole repaired.

Devices and methods have been described for suturing such holes to close them. However, such devices and methods are commonly very difficult to use in such limited spaces. To avoid sutures, devices have been developed to plug or cover such holes, to allow the hole to heal naturally or incorporate some or all of such plugs into the tissue. Such items have been effective, but may be difficult to place, particularly when both sides of a hole must be closed.

The present disclosure addresses these problems.

SUMMARY

Among other things, there is disclosed a closure device including a distal collapsible mesh element, a proximal collapsible mesh element, and a tether or stem that connects and is used to pull the two mesh elements together, sandwiching a hole to be sealed. The distal mesh element has two ends that are inverted into the mesh body interior. The mesh fibers at each of the ends are fused together or otherwise narrowed with a bonding or fusing operation such as shape-setting with heat. Radiopaque markers (e.g. cylindrical markers) may be embedded in the fused ends. In particular embodiments, these ends are both inverted into the body of the distal mesh element. The distal end of the distal mesh element is used to anchor the distal end of the tether or stem. The proximal end of the distal mesh may be covered (internally or externally) with a material to seal and/or promote healing (e.g. small intestine submucosa [SIS]).

The proximal mesh element has a distal end that is inverted into the body of the proximal mesh element. The end is fused in an identical or similar manner to the ends of the distal mesh element and may also have a radiopaque marker. The distal end of the proximal mesh element may also be covered (internally or externally) with a material to seal and/or promote healing. In particular embodiments, the proximal end of the proximal mesh element is also fused or otherwise narrowed and incorporates a radiopaque marker, but is not inverted. The proximal fused or narrowed end serves as an eventual conduit for the tether.

The tether has a distal end, which may be enlarged (e.g. with a bead, node or knot) and may be fixed to the distal end of the distal mesh element, has a cross-sectional enlargement (e.g. a bead, node or knot) at or near its proximal end. The tether also has a loop feature in particular embodiments that is a part of or adjacent to that proximal enlargement to allow attachment to a trigger or control wire. The wire is used to pull the tether through the proximal end of the proximal mesh element as a delivery tool or device pushes and compresses the proximal mesh element. The proximal enlargement is pulled through the fused proximal end of the proximal mesh element and provides a lock or stop for the proximal mesh element once tension on the tether is released.

The delivery tool delivers the mesh elements in a stacked manner. The closure device is stacked within the tool with the distal mesh element residing in a distal peel-away catheter (e.g. 14 French), and the proximal mesh element residing in a sheath (e.g. 12 French). When the tool is inserted into a sheath through the hole to be closed, which is anchored by a balloon on the distal side of the hole, the peel-away catheter is removed so that the distal mesh element sits within the sheath through the hole and is pushed by the sheath holding the proximal mesh element. The distal mesh element is pushed out of the sheath through the hole to a site distal to the hole to be sealed. The tether is then slightly retracted which serves to compress the distal mesh element against the sheath holding the proximal mesh element. The distal mesh element is thereby expanded. After deflating the balloon, the two sheaths are pulled back through the hole, which pulls the distal mesh element against the tissue and seals the hole.

In embodiments in which one or both sheaths include a fluid pathway, a contrast medium may be moved through that pathway to the site to allow visualization (e.g. by fluoroscopy) so as to check the seal created by the distal mesh element. After confirming a seal, and confirming that the sheath tips are on the proximal side of the hole, the proximal mesh element is pushed out of its sheath with a smaller inner tube or sheath (e.g. 9 French), alone or with further retraction of the sheath that held the proximal mesh element. Tension is maintained on the tether or stem via the control wire throughout to ensure that the distal mesh element maintains a seal of the hole. The inner tube or sheath continues to push the proximal end of the proximal mesh element so as to advance that proximal end over the control wire and ultimately over the proximal enlargement on the tether or stem, locking the mesh elements together. A final contrast injection can be made to confirm the seal of the hole, and an end of the control wire is released to allow it to unloop from the tether or stem end.

In particular embodiments, the tether or stem may have multiple enlargements (e.g. knots, beads or nodes) to allow variable amounts of tightening of the mesh elements together. The proximal end of the proximal mesh element may have reliefs cut into it to allow some expansion as enlargement(s) of the tether or stem are pulled through that proximal end, and/or have a tapered hole to favor unidirectional movement of the tether or stem enlargement(s) through. Other gripping, attachment or reversion preventers or minimizers may be used, such as a barb, claw or corkscrew in the proximal end of the proximal mesh element to engage the tether or stem. A handle of the delivery device or tool may have one or more actuators or other mechanisms to promote performing deployment steps in the proper order and to minimize the chance of premature deployment or release of any component during the procedure.

As examples, a closure for an opening in tissue can include a first closure element, the first closure element having a first mesh enclosure, the first mesh enclosure having a first distal narrowed end and a second proximal narrowed end and a central volume. Each of the first and second ends are inverted so as to be within the central volume of the first mesh enclosure, and each of the first and second ends are surrounded by respective external surfaces of the first mesh enclosure. A second closure element has a second mesh enclosure with a third distal narrowed end and a fourth proximal narrowed end and a central volume. The third end is inverted so as to be within the central volume of the second mesh enclosure, and each of the third and fourth ends are surrounded by respective external surfaces of the second mesh enclosure. A tether joins the first and second closure elements in an initial configuration prior to delivery of the closure elements to the opening. The tether has first and second enlarged ends, wherein the tether extends through the first, second and third narrowed ends so that the first enlarged end of the tether is outside the first closure element adjacent or engaging the first end and the second enlarged end of the tether is within the central volume of the second closure element. The first closure element is adapted to engage a distal side of the tissue having the opening, and the second closure element is adapted to engage a proximal side of the tissue, and the tether is adapted to pass through the opening.

The mesh for the closure elements and the material for the tether or stem are preferably bioresorbable. As the closure elements are formed or prepared, a heat-annealing or shape-set process may be performed on them so that even though compressed or otherwise fitted within a delivery device, the closure elements naturally expand when deployed from the delivery device.

A sheet of bioresorbable material may be fixed to the first closure element adjacent or over the second narrowed end. Such a sheet can be fixed to an external portion of the first mesh enclosure. The enlarged ends of the tether can be or include a bead or a knot. A control wire is looped through the second enlarged end of the tether, and may pass through the fourth narrowed end. The closure device is preferably initially fitted within a delivery device. The ends of the first closure element may be aligned with each other, and/or the ends of the second closure element may be aligned with each other. In other embodiments, the ends of the first closure element may be laterally offset with respect to each other, or one of those ends may be larger in diameter than the other.

An example of a device for closing an opening in tissue can include a delivery device having a first peel-away catheter, a second tube within the first peel-away catheter, and a pusher tube within the second tube, along with a closure device as disclosed herein fitted within the delivery device. For instance, a first closure element may be within the first peel-away catheter and a second closure element within the second tube. A control line may be looped through the second enlarged end of the tether. A control cannula may extend through the pusher tube, with the control line extending through the control cannula. The control line can extend from the control cannula and returns to the control cannula from the second enlarged end of the tether, so that a free end of the control line is within the control cannula.

BRIEF DESCRIPTION OF THE DRAWINGS

FIG. 4 is a side part-cross-sectional view of a portion of the embodiment of FIG. 1 with an alternative joining member.

FIG. 5 is a side part-cross sectional view of an alternative closure element that can be used in the embodiment of FIG. 1.

FIG. 6 is a side part-cross sectional view of an alternative closure element that can be used in the embodiment of FIG. 1.

FIG. 7 is a side part-cross sectional view of an alternative closure element that can be used in the embodiment of FIG. 1.

FIG. 8 is a side part-cross-sectional view of a delivery device with the embodiment of a closure device of FIG. 1 fitted within it, in an initial stage of insertion into a patient.

FIG. 9 is a view of the embodiment of FIG. 8 in a later stage of deployment compared to FIG. 8.

DESCRIPTION OF THE ILLUSTRATED EMBODIMENT

Figure 1:
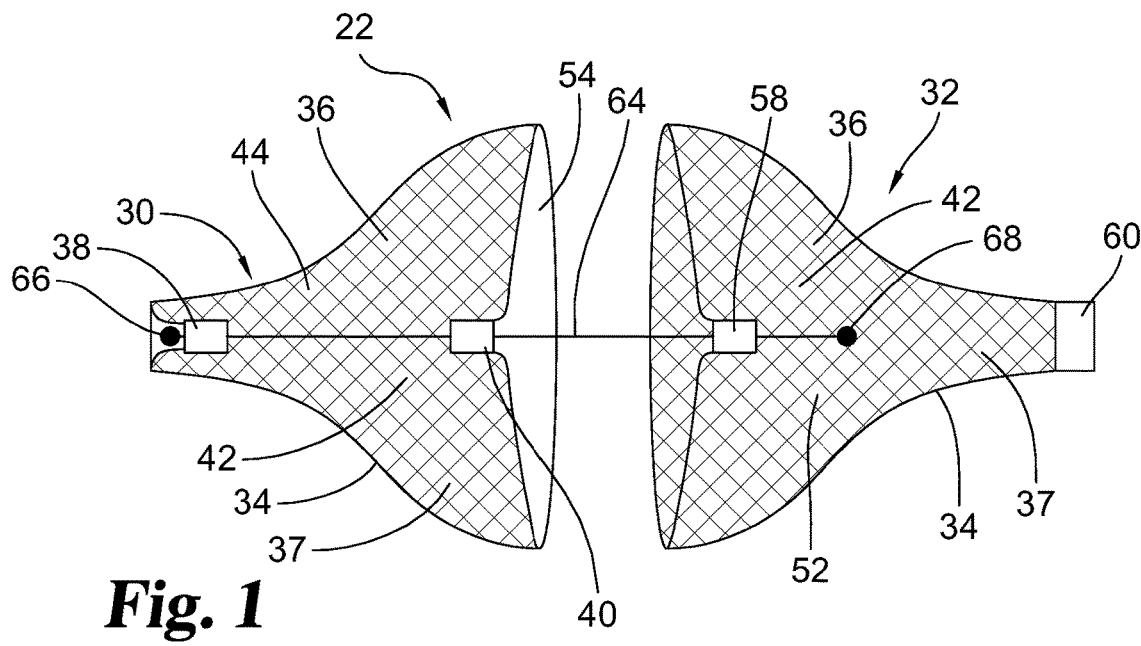
FIG. 1 is a perspective view of an embodiment of a closure device described herein.
Figure 2:
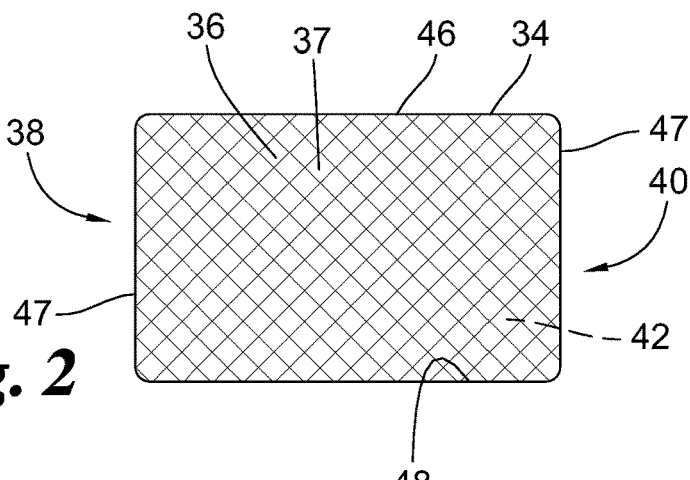
FIG. 2 is a side view of an embodiment of a mesh portion prior to being formed into a part of the embodiment of FIG. 1.
Figure 3:
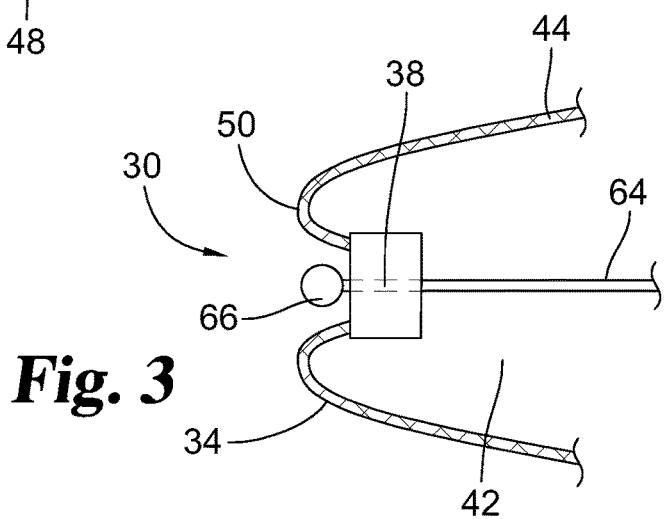
FIG. 3 is a side part-cross-sectional view of a portion of the embodiment of FIG. 1.
Figure 10:
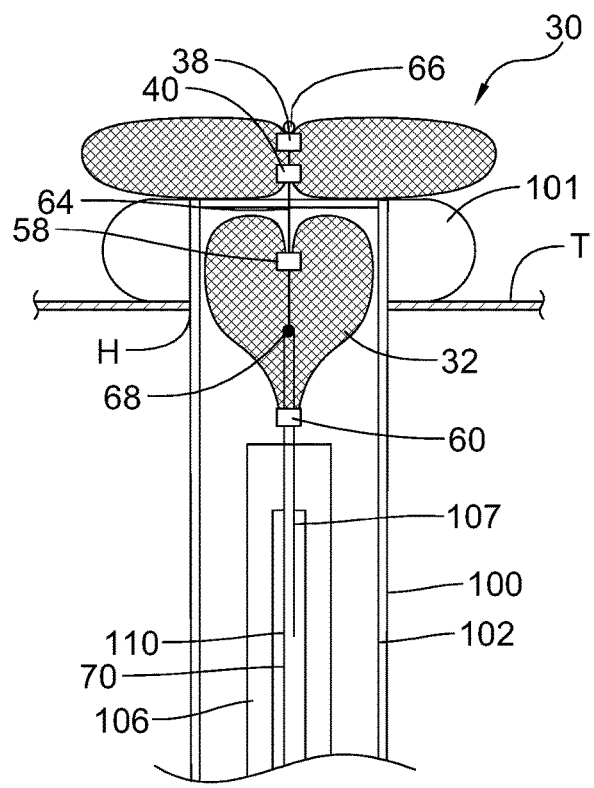
FIG. 10 is a view of the embodiment of FIG. 8 in a later stage of deployment compared to FIG. 9.
Figure 11:
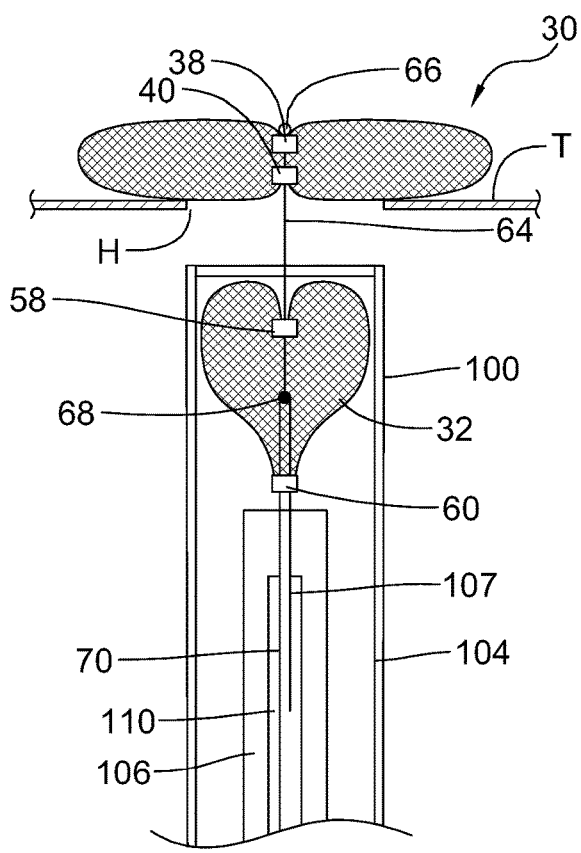
FIG. 11 is a view of the embodiment of FIG. 8 in a later stage of deployment compared to FIG. 10.
Figure 12:
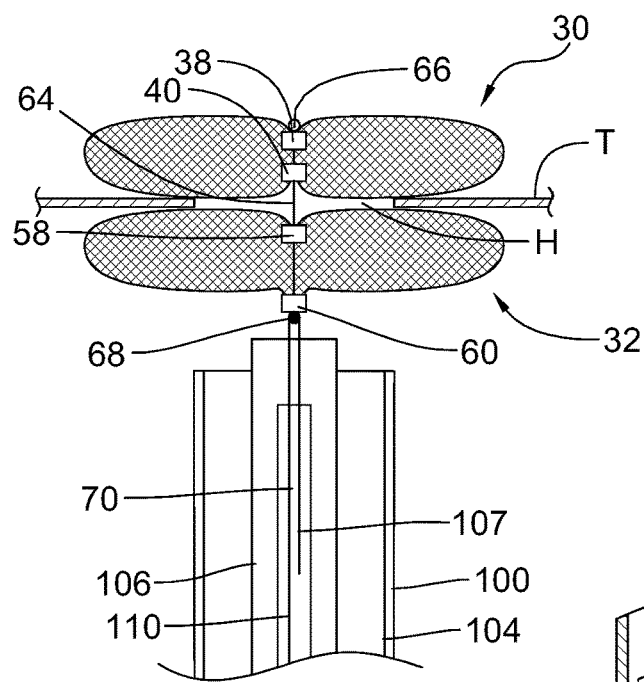
FIG. 12 is a view of the embodiment of FIG. 8 in a later stage of deployment compared to FIG. 11.

For the purposes of promoting an understanding of the principles of the disclosure, reference will now be made to the embodiments illustrated in the drawings and specific language will be used to describe the same. It will nevertheless be understood that no limitation of the scope of the claims is thereby intended, and alterations and modifications in the illustrated devices and methods, and further applications of the principles of the disclosure as illustrated therein are herein contemplated as would normally occur to one skilled in the art to which the disclosure relates.

Referring generally to the drawings, there are shown embodiments of parts of a system 20 for closing a hole in tissue, for example cardiac tissue. Such a system may include one or both of a closure device 22 and a placement device 24. As will be discussed further below, closure device 22 is initially placed within placement device 24. When placement device 24 is adjacent or through a tissue opening, closure device 22 is moved out of placement device 24 to cover the tissue opening, and is fixed in place to permit or promote healing.

Closure device 22 in the illustrated embodiment is a two-piece device, having a first or distal closure element 30 and a second or proximal closure element 32. "Distal" and "proximal" in this context refers to relative position with respect to the direction of travel of closure device 22 and/or placement device 24, "distal" being generally toward or beyond a tissue hole or opening to be closed, and "proximal" being generally toward the operator along that direction of travel. Closure element 30 is intended to engage tissue and cover an opening through it on the distal side of the tissue, i.e. the side beyond a hole through the tissue. Closure element 32 is intended to engage tissue and cover an opening through it on the proximal side of the tissue, i.e. the side approached first by placement device 24. Closure elements 30 and 32 are linked together prior to insertion into a patient's body or on or into a delivery device in particular embodiments, as discussed further below.

Closure element 30 in the illustrated embodiment is made of a mesh 34, and in particular embodiments are bioresorbable, non-bioresorbable, and/or of a biologic material. Such materials may be or include polypropylene, polyethylene, glycolide/L-lactide copolymer, PTFE, nylon, polyurethane, PEEK, PLGA, PGA, polycaprolactone, carbothane, polydioxanone, or copolymers of such constituents. Mesh 34 as illustrated includes a number of interstices 36 among a solid but flexible material that are or have the appearance of crossed strand(s) or similar linear member(s) 37.

Closure element 30 has first and second ends 38, 40 in the illustrated embodiment which are narrowed or closed. In one example, a sheet or length of mesh 34 is rolled or otherwise formed around an axis into a cylinder or other longitudinally closed shape having opposing open ends 38 and 40. In such embodiments, mesh 34 has a central volume 42 between ends 38 and 40. End 38 is narrowed or closed to form a tube (e.g. with a passage), a closed mass, or other tip. For example, narrowing or closing can be accomplished by heat-shrinking a portion of end 38 to form a tube with a passage having a diameter substantially smaller than a nominal diameter of central volume 42, e.g. one-third to one-tenth of such nominal diameter or smaller. As another example, narrowing or closing can be accomplished by chemically or thermally fusing end 38 to form a closed mass as a tip. Techniques such as those described in US Patent Application Publication No. 2015/0374475 (incorporated herein by reference in its entirety) may be used. End 40 is similarly narrowed or closed, preferably to form a tube with a small passage through it. Closure element 30 thus has an intermediate portion 44 of mesh 34 longitudinally in between narrowed or closed ends 38 and 40, with volume 42 being within intermediate portion 44 and bounded by mesh 34.

In particular embodiments, end 38 (and potentially other end(s) of closure elements 30, 32) is or includes a radiopaque marker. For example, such a marker may be a tube of biocompatible metal (e.g. gold, platinum, tungsten-, zinc-, iron-, and/or magnesium-based metals) or appropriate bioresorbable materials. Exemplary markers have open ends and an interior and exterior, and in some embodiments include a side opening through a side wall. It is encased by mesh 34 of the particular closure element. Such integration is possible where the mesh 34 is able to exist as a fluid mass and can undergo a phase change to a solid mass. With end portion of mesh 34 treated to become a fluid mass (as by heating, chemical curing, or applying electric or magnetic fields), pressure is applied to direct the fluid mass into and around the tubular marker, e.g. in or through the open ends and/or the side opening. The fluid mass then undergoes a phase change to solid (as by cooling) so that the solid mesh material encases the tubular marker. The interior of the marker may be occluded by the mass entirely, or a lumen can be left through the encased marker. In this way, the marker is securely anchored with respect to the mesh 34 while covering any rough edges on the marker. Such markers serve to indicate when the ends of one or both of closure elements 30, 32 are pulled together, e.g. to indicate the shape of the compressed or collapsed mesh and indicate if the mesh compression is distorted.

Closure element 30 in the illustrated embodiment is double-inverted, meaning that each end 38, 40 is inverted so that the narrowed or closed portions point into or are within volume 42. For example, closure member 30 may be made by forming a sheet of mesh 34 into a tube with open ends (which will become ends 38 and 40). In that tube form, there is an exterior surface 46 with edges 47 surrounding an inner space, which will form the volume 42 of closure member 30. An interior surface 48 faces that volume 42. Forming an inverted end includes turning the edge 47 into the inner space, so that the edge is inside of a portion of the interior surface 48. The end is narrowed or closed, as noted above (e.g. by heat-shrinking, chemical treatment), so that the edge remains inside volume 42 of closure 30. In such an example, a portion of the exterior 46 of the mesh 34 folds over itself, and a curved or folded part of that exterior 46 forms an exterior end 50 of closure 30, with end 38 inverted into volume 42. It will be understood that the narrowing or closing of the end(s) can occur prior to or after inversion. As noted, closure element 30 is double-inverted, so that end 40 is also inverted identically or similar to end 38.

In particular embodiments, some or all of closure element 30 includes a sheet or mass of therapeutic or healing material 54, which may at least partially block fluid flow and/or assist in tissue growth and contribute or assist the healing process. As an example, a sheet, layer or other portion of SIS (small intestinal submucosa) may be placed to line the inside of mesh 34 (e.g. within volume 42) or fixed to an outside portion of mesh 34. A layer 54 is indicated in FIG. 1 fixed to the outside of mesh 34 to cover most or all of the surface around end 40, or at least so that when closure element 30 is flattened as discussed further below, the sheet 54 covers at least part of a tissue opening to be repaired or healed.

Closure element 32 is for proximal placement, i.e. on the side of the tissue that is first reached or approached by placement device 24, and is similar to closure element 30 in particular embodiments. For example, closure element may be identical or essentially identical to closure element 30 as described above, having mesh 34 as a body enclosing a central volume 52, with first and second ends 58, 60 in the illustrated embodiment which are narrowed or closed. In a particular embodiment, closure element 32 is similar to closure element 30 as described above, but has one inverted end 58 and one non-inverted end 60 (see FIGS. 1, 4). End 58 is inverted and closed or narrowed as described above. End 60 is closed or narrowed as described above, but an exterior surface of mesh 34 of closure element 32 is not folded in on itself, and so end 60 does not enter or point into volume 52. Rather, in this embodiment end 60 points generally away from volume 52. In a particular embodiment, ends 58 and 60 are aligned along a common longitudinal axis that extends through volume 52. It will be understood that in other embodiments closure element 32 is double-inverted, like closure element 30, rather than single-inverted.

Closure elements 30 and 32 are joined by a filament or tether 64 in specific embodiments. Tether 64 has two ends 66, 68 that are enlarged, as with knots or beads, that are at least slightly larger than any opening through ends 38, 40, 58, 60 of closure elements 30, 32. Additional beads, knots or other enlarged portions may be present between ends 66 and 68 for adjustability in locking closure elements 30, 32. Tether 64 extends through end 38 of closure element 30, with end 66 of tether 64 outside of volume 42 and within, engaged with or beyond end 38 of element 30, so as to be fixed or otherwise connected to end 38. From end 38, tether 64 passes through both ends 38 and 40 and volume 42 of element 30. From closure element 30, tether 64 extends across any gap that may exist between closure elements 30 and 32, and then passes through end 58 and into volume 52 of closure element 32. It will be understood that in embodiments in which tether 64 is fixed to end 38 of closure element 32, other ways of fixation such as adhesives or fusion, could be used to fix tether 64 to end 38 or another part of closure element 30. In the illustrated embodiment, tether 64 is connected to end 38 at a point within the inner space created by the fold of the inversion of end 38. Tether 64 is not fixed with respect to end 40 of closure element 30, but can be moved through end 40, as by pulling. Likewise, tether 64 is not fixed to end 58 of closure member 32, but can be moved through ends 58 and end 68 of tether 64 can be forced through end 60 of closure element 32, as by pulling. Pulling on tether 64 can collapse closure member 30 toward closure member 32 and toward tissue between members 30 and 32.

As will be discussed further below, a tensioning or control line 70 is looped through end 68 of tether 64, passing into and out of closure element 32 via the opening through end 50 of closure element 32. In particular embodiments, line 70 passes through a bight, hole or knot in tether 64. When line 70 is pulled or otherwise placed in tension, it places tension on tether 64 and thereby pulls on end 38 of closure member 30, pulling or flattening closure member 30 toward tissue and closure member 32. Control line 70 is also a part of the procedure to flatten closure element 32 with respect to tissue, as will be discussed further below.

In an alternative embodiment, a filament in the form of a solid stem 64' is provided in place of tether 64. Stem 64' in the illustrated embodiment has an elongated body 65' with a flat end 66' and an opposite end 68'. In the illustrated embodiment body 65' and ends 66' and 68' are monolithic, e.g. formed or created as a single piece of the same material. Such materials are preferably a bio-resorbable material that has sufficient strength to hold the two closure elements 30, 32 together for a time sufficient to allow the closure elements 30, 32 to be encapsulated and sealed by bodily tissue. Body 65' includes one or more protrusions 69' to act as stop points or barbs between end 68' and flat end 66'. In particular embodiments, protrusions 68' have surfaces facing flat end 66' that are perpendicular to or form an acute angle with a longitudinal axis of body 65', to form stop surfaces as will be discussed further below. End 68' is adapted to be engaged to a suture or control line 70 (as discussed further below), for example having a loop, bight or eye through which control line 70 can extend and/or be attached to body 65'. Flat end 66' in a particular embodiment is substantially planar along a surface 71' that adjoins body 65', and convexly curved along a surface 72' opposite surface 71'.

In this embodiment, stem filament 64' is fixed to or otherwise engaged with closure member 30. For example, body 65' is inserted through the closed or narrowed end 38 of closure member 30, with flat end 66' abutting a portion of closure element 30 that is distal of the inverted end 38 so as to anchor stem 64 to the closure element 30. Body 65' extends through closure element 30 and into or through closure element 32 in an initial condition, and is adapted to extend through and away from end 50 of closure element 32 when placed in the body. In particular embodiments, body 65' can extend through each of ends 38, 40, 58, 60 of the closure elements 30, 32, and in other embodiments body 65' need not pass through one or more of those ends, but can pass through the mesh of one or more parts of closure elements 30, 32.

When closure device 22 is initially prepared, end 68 of tether 64 or protrusions 69' of body 62' extend at least through end 38 and into volume 42 of closure element 30. Control line 70 extends from tether 64 or body 65', and depending on how far tether 64 or body 65' is initially placed through closure element 30 and/or 32, line 70 extends through closure element 30 and 32, exiting closure element 32 via narrowed or closed end 60. As closure elements 30, 32 are being placed, they are compressed so that tether 64 or stem 64' holds one or both of them in a compressed state. For example, once closure element 30 is placed (as discussed further below), line 70 may be pulled, so that tether 64 or stem 64' is pulled, and end 66 of tether 64 or one or more protrusions 69' of body 65' are forced through end 60 or another portion of closure element 32. End 66 of tether 64 or flat end 66' of stem 64' pulls the distal portion (or end 38) of closure element 30 toward the proximal portion (or end 40) of closure element 30, compressing closure element 30. One or more protrusions 69' can engage a proximal portion (or end 40) of closure element 30 to prevent re-expansion of closure member 30. Similarly, further pulling of line 70 can draw body 65' through a distal portion (or end 58) of closure element 32 and/or through a proximal portion (or end 60) of closure element 32 to compress closure element 32 on itself and/or toward closure element 30, to finally fix closure device 22 against tissue. Thus, tether 64 or stem 64' passes between and within closure elements 30, 32, with end 66 of tether 64 or flat end 66' of stem 64' on the distal outside of closure element 30, and at least one protrusion 69' of body 65' on the proximal outside of closure member 32.

The inventors have further found that there is an advantage in some uses of closure device 22 of reducing the compressed, in-use height of one or both of closure elements 30, 32. By "height" in this context is meant the dimension measured outward from the tissue to which the closure elements are applied. To address those cases where space is minimal or where a smaller closure is otherwise indicated, closure element 30 is prepared so that ends 38 and 40 are offset from each other within volume 42. As seen in FIG. 5, ends 38 and 40 are inverted and narrowed or closed as described above but are arranged non-symmetrically, so that each end 38, 40 is to one side of the other. This allows closure element 30 to be compressed so that ends 38 and 40 move past each other, with less or no contact or other interference with each other as compared to a configuration as described above in which ends 38, 40 are aligned or coaxial. In this embodiment, tether 64 or stem 64' is fixed to end 38, as discussed above, but does not extend through end 40. Rather, tether 64 or stem 64' passes through mesh 34 alongside end 40, and on to closure element 32, as discussed above. It will be understood that a similar configuration could also or instead be applied to closure element 32.

In another embodiment (FIG. 6), closure element 30 has ends 38 and 40 that are aligned, but with one of the ends 38 or 40 of a larger diameter than the other. For example, end 40 is inverted and narrowed as discussed above, to a given diameter. End 38 is inverted and narrowed as discussed above to a diameter smaller than that of narrowed end 40. Tether 64 or stem 64' extends through both ends 38 and 40. When closure element 30 is compressed, end 38 is pulled toward end 40 so that end 38 enters at least partially into end 40. It will be understood that in other embodiments end 40 may be smaller than end 38, and that similar configuration(s) could also or instead be applied to closure element 32.

In another embodiment (FIG. 7), closure element 30 is not a double-inverted member, but is instead a single-inverted member like the illustrated embodiment of closure element 32. Thus, in this embodiment end 38 is inverted as discussed above, but end 40 is not inverted, like end 60 of closure element 32. One or both of ends 58, 60 of closure element 32 have a diameter greater than that of end 40 of closure member 30, as in the above discussion. Tether 64 or stem 64' passes through each of ends 40 and 58 initially, and in use through end 60, in this embodiment. When closure elements 30, 32 are compressed, end 40 of closure element 32 passes through the tissue hole to be closed or sealed, and may enter one or both of ends 58, 60 of closure element 32.

Closure device 22 may be placed in the body in a minimally-invasive manner, e.g. by obtaining percutaneous access to a blood vessel, organ or other part of the body and moving closure device 22 with or through a catheter or other tube to the desired location. It will be understood that closure device 22 may be placed at the desired location in the body via open surgery or other procedures as well. An embodiment for placement device 24 for minimally-invasive placement of closure device 22 is shown schematically in FIGS. 8-13. This embodiment of placement device 24 is intended for insertion through a previously placed sheath 100 that allows access to or is placed through a hole H in tissue T to be closed. In this example, sheath 100 extends from within a right atrial appendage (RAA) through hole H in tissue T to the pericardial space, in which balloon 101 of sheath 100 is inflated to anchor sheath 100.

Device 24 includes three tubular members 102, 104 and 106 to which a handle 108 is connected, in the illustrated embodiment. As will be discussed further below, device 24 is inserted through delivery sheath 100, which in one example is a 14 French tubular sheath that has been advanced through and anchored with respect to hole H. In that example, tubular member 102 is a 14 French peel-away tube around and at the distal end of member 104, which can be a 12 French delivery sheath. Member 106 is a pusher and/or guide cannula, which is slidable within member 104. Thus, member 104 is initially at least partially inside peel-away member 102, and member 106 is within member 104. In particular embodiments, a further tubular member 110, extending through member 106, is provided as a guide cannula for control line 70. Control line 70 extends through member 110, and in a particular embodiment line 70 is a thin braided stainless steel cable. Line 70 has a proximal end connected to handle 108, and extends out of the open distal end of member 110, through end 60 of closure element 32, looping through tether 64 or stem 64' (as discussed above), and returning through end 60 and into member 110. In this way, line 70 is doubled initially within member 110, so that a free end 111 is in member 110 and generally points proximally. Member 104 can fit into sheath 100 while containing closure device 22. In an initial (pre-usage) configuration, closure element 30 is within member 102, and closure element 32 is within member 104, which is immediately or closely adjacent closure element 30. Pusher member 106 is initially proximal or rearward of closure element 32. As device 24 is inserted into the delivery sheath 100, peel-away member 102 is pulled apart and removed, leaving closure member 30 within sheath 100, and delivery member 104 (with closure element 32 inside) behind closure element 30 and also within sheath 100.

Embodiments of system 20 (e.g. placement device 24 and/or one or both of closure elements 30, 32) can be configured to accommodate passage of a wire guide. For example, such a wire guide may run through each closure element 30, 32 and through placement device 24 and into sheath 100 that is in hole H. The wire guide may run alongside or within the pusher member 106, or may run through a separate lumen through or alongside device 24. If the wire guide passes through closure elements 30, 32, it may do so through mesh 34 at location(s) other than at one or more of ends 38, 40, 58, 60. Such a wire guide serves both to help align the closure elements 30, 32, and to provide a navigation pathway that may be left behind in the event that use of system 20 needs to be abandoned and the closure process re-started. In such a case, the wire guide provides a guide path for subsequent closure devices to approach and close hole H.

As noted, the illustrated embodiment of sheath 100 includes a balloon 101 at or near a distal end, to anchor delivery sheath 100. When sheath 100 extends through a hole, to deliver therapeutic devices or compositions or for other purposes, balloon 101 is inflated on the distal side of the hole in order to anchor delivery sheath 100 in place. With sheath 100 so anchored, and all desired procedures via sheath 100 having been performed, the user inserts placement device 24 in its initial configuration into sheath 100 and peels away member 102, as indicated above. Such insertion and advancing into sheath 100 may be accomplished over a wire guide that passes through or along device 24. Device 24 without member 102 (i.e. members 104 and 106, connected to handle 108 and including the features noted above within members 104 and/or 106) is then pushed through sheath 100 so that closure element 30 emerges from the distal end of sheath 100. In particular embodiments, moving delivery member 104 forward from or using handle 108 pushes closure element 30, so that closure element 30 is pushed outside of sheath 100. Member 104 and/or handle 108 connected to it is preferably locked to sheath 100 outside the patient's body, and deployment of closure element 30 can be visualized (e.g. by fluoroscopy).

When closure element 30 has emerged from member 104, distal end 38 is generally away from tissue T through which hole H extends. End 40 is directed toward tissue T, so that exterior end 50 (with folded-over mesh and in some embodiments healing material, as noted above) faces hole H. Tension is maintained on tether 64, by pulling back at least slightly on member 110 (which may be connected to or locked with members 104 and/or 106). Such pulling provides tension via control line 70 to tether 64 and on to end 38 of closure element 30, flattening closure element 30 against the distal end of sheath 100.

At this point, balloon 101 is deflated to permit withdrawal of sheath 100 from hole H. Sheath 100 and device 24 are withdrawn together until closure element 30 engages the distal surface of tissue T (e.g. the pericardial side of the RAA wall). Again, the user can visualize the site to confirm that closure element 30 is against the tissue and/or to confirm that sheath 100 is out of hole H (e.g. fully on the cardiac side of the RAA wall). The position of member 106 (e.g. with member 110) and line 70 is then maintained as member 104 and sheath 100 are withdrawn further to expose and deploy the middle of tether 64. The user can confirm (e.g. by visualization under fluoroscopy) the spacing between closure element 30 and the distal end of member 104 and/or that the distal end of member 104 is clear of the RAA wall. Again maintaining the position of member 106 (e.g. with member 110) and line 70, member 104 and sheath 100 are further withdrawn to expose and deploy closure element 32 from within member 104. Visualization of that deployment can be performed.

With closure element 32 out of member 104 and its distal end 58 generally facing tissue T, the operator holds the position of line 70 while advancing pusher member 106 against proximal end 60 of closure element 32. Member 106 pushes end 60 over enlarged end 68 of tether 64, forcing end 68 through end 60 and flattening closure element 32. As noted above, enlarged end 68 of tether 64 is larger than an opening through end 60 of closure element 32, so that once tether end 68 is forced through end 60, closure device 22 is locked. That is, closure elements 30 and 32 are flattened against their respective sides of tissue T, and tether 64 locks them together, preventing ends of the closure elements from passing over enlarged ends 66, 68 of tether 64.

With closure device 22 locked, line 70 is maintained in position while member 110 is withdrawn sufficiently to allow the free end 111 of line 70 to escape the distal end of member 110. Line 70, as noted above, is looped so as to have free end 111 within member 110, and in particular embodiments, free end 111 bends outward when free of member 110. With free end 111 outside of member 110, line 70 is withdrawn (e.g. via handle 108). Free end 111 is pulled through end 68 of tether 64 and from closure element 32, and away from the treatment site. The remainder of device 24 (including members 104 and 106) and sheath 100 can then be withdrawn, over a wire guide if present. Closure device 22 remains in the above-noted locked condition to allow healing of hole H.

Figure 13:
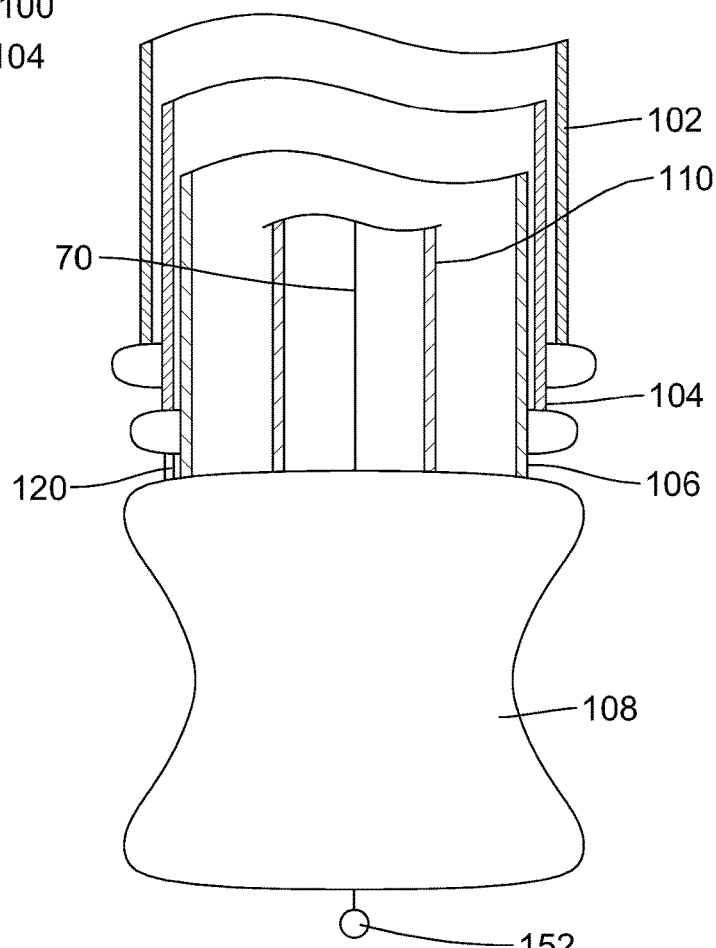
FIG. 13 is a schematic representation of a portion of the delivery device embodiment shown in FIG. 8.
Figure 14:
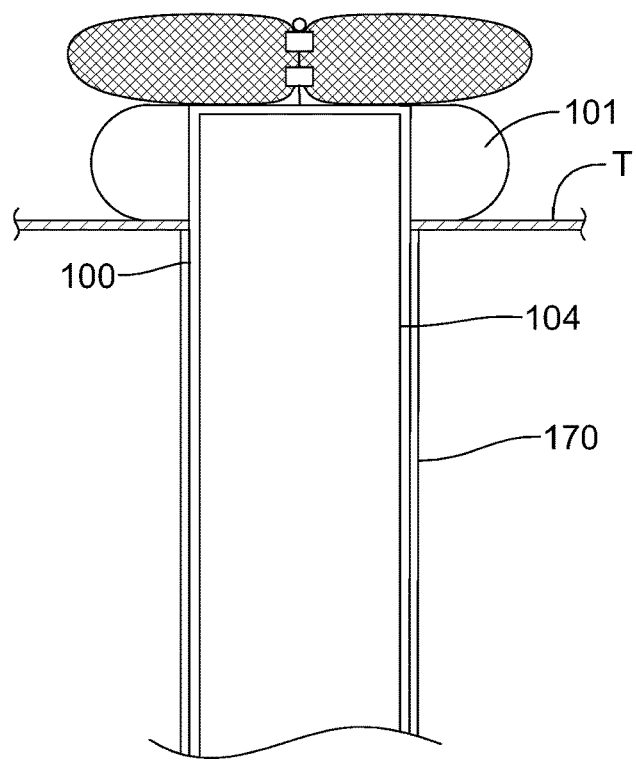
FIG. 14 is a side part-cross-sectional view of a portion of the delivery device embodiment of FIG. 8 with additional structure.
Figure 15:
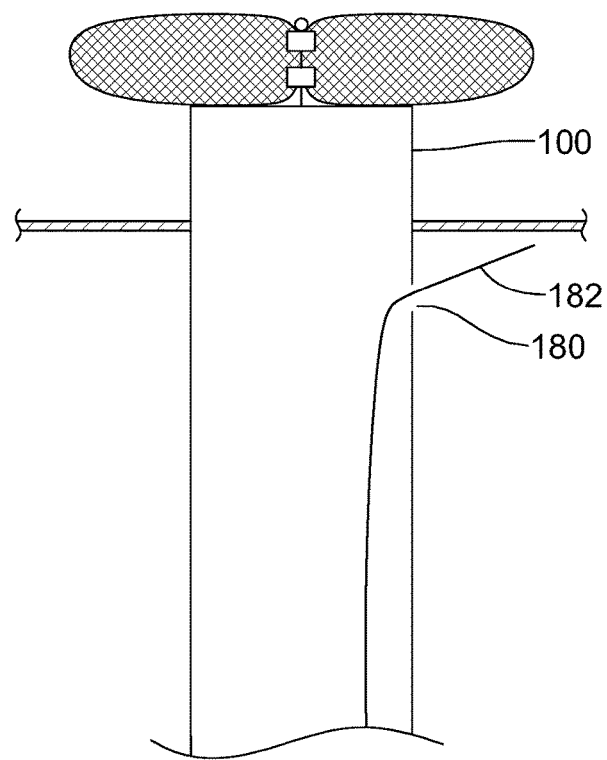
FIG. 15 is a side part-cross-sectional view of a portion of the delivery device embodiment of FIG. 8 with additional structure.

An exemplary embodiment of the operational (distal) end of device 24 is shown schematically in FIG. 13. Peel-away sheath 102 is shown as outermost, with distal closure element 30 within it. An inner catheter or tube 104 is within peel-away sheath 102, and its distal end is closely adjacent to closure element 30. Proximal closure element 32 is within inner catheter or tube 104. A pusher or guide tube or cannula 106 is within inner catheter or tube 104, and in particular embodiments a cannula 110 for control line 70 is provided. Control line 70 extends through member 106 and/or member 110, is threaded through end 68 of tether 64, and returns to member 106. Proximally, each of members 104, 106 (and member 110 if present) and line 70 are connected to handle 108.

The representation of handle 108 shows pusher catheter 106 connected directly to it, with peel-away sheath 102 and inner catheter or tube 104 around pusher catheter 106. A lock 120 may connect handle 108 and tube 104 in particular embodiments. The connection of handle 108 and line 70 is not shown in that figure. In the illustrated embodiment, handle 108 includes a body 150 shaped and configured for holding and maneuvering by hand. Three actuators are placed on or in handle 108. A control line actuator 152 may include a pull ring and a shaft connected to line 70. Actuator 152 maintains line 70 in position, and by pulling actuator 152, line 70 is pulled or placed in tension. Additional actuators may be connected to members 104 and/or 106 to permit relative motion of them with respect to each other or other parts of device 24. It will be understood that one or more actuators can be assembled in series to automate several actions with essentially one motion.

One problem that has occurred with placement of delivery sheaths or similar devices through tissue openings is that when the sheath is withdrawn, the friction of the withdrawing sheath can stretch or move the tissue plane through which the opening extends. For example, in an procedure in which a hole is created in the thin wall of the right atrial appendage for a delivery sheath, when the sheath is withdrawn through the hole the appendage wall will tend to invaginate into the right atrium, which is undesirable. To address that problem, an outer sheath 170 may be placed over the delivery sheath (100 in the illustrated embodiment) that is anchored by a balloon 101. While balloon 101 is inflated, sheath 170 is moved to a position so that its distal end is just proximal to the hole (e.g. engaging or closely adjacent to tissue around the hole). When the delivery sheath 100 is withdrawn (following deflation of balloon 101), the distal end of sheath 170 supports the wall of the tissue plane through which sheath 100 is withdrawn.

Alternatively, delivery sheath 100 may include a lumen (either the same or a different lumen from that containing device 24) and a communicating side port 180 located a sufficient distance below balloon 101 to be at least partially below an inner tissue wall surface when balloon 101 is inflated and anchoring on the outer tissue wall surface. A wire 182 fabricated from a shape-memory material (e.g. Nitinol) is within the lumen in an unexpanded or restrained shape or configuration. When withdrawal of sheath 100 is desired, wire 182 is advanced through the lumen and at least partially out of port 180. As wire 182 emerges from port 180, it assumes an expanded shape, e.g. an expanding helical shape. Wire 182 presses against the wall of the tissue plane as it is advanced, providing counter support for the tissue as the sheath 100 is withdrawn.

It will be understood that port 180 may also be used for other purposes, in addition to or instead of placement of wire 182. For example, once sheath 100 is in place or close to it, a contrast medium can be injected through the lumen and the side port 180 to help visualize the hole or tissue surrounding it. Similarly, side port 180 may be used as a flush port.

The above discussion of closure of a hole in an organ or other tissue is generally applicable to a number of types of openings, whether occurring naturally (e.g. a fistula) or artificially (e.g. through trauma or for passage of a therapeutic or diagnostic device). In particular embodiments, as noted above, the devices and methods described herein can be used for repairing a hole through a right atrial appendage opened for passage of treatment devices to the heart. In such an embodiment, the tissue T is part of the right atrial appendage, separating the appendage's interior from the pericardial space.

While the subject matter herein has been illustrated and described in detail in the exemplary drawings and foregoing description, the same is to be considered as illustrative and not restrictive in character, it being understood that only the preferred embodiment(s) have been shown and described and that all changes and modifications that come within the spirit of the disclosure are desired to be protected. It will be understood that structures, methods or other features described particularly with one embodiment can be similarly used or incorporated in or with respect to other embodiments.

What is claimed is:

1. A closure for an opening in tissue, comprising:
    a first closure element, the first closure element having a first mesh enclosure, the first mesh enclosure having a first distal narrowed end and a second proximal narrowed end and a central volume;
    a second closure element, the second closure element having a second mesh enclosure, the second mesh enclosure having a third distal narrowed end and a fourth proximal narrowed end and a central volume;
    a tether joining the first and second closure elements in an initial configuration prior to delivery of the closure elements to the opening, the tether having first and second ends, wherein the first distal narrowed end of the first closure element is configured to anchor the first end of the tether and the second end of the tether is within the central volume of the second closure element,
    wherein the first closure element is adapted to engage a distal side of the tissue having the opening, and the second closure element is adapted to engage a proximal side of the tissue, and the tether is adapted to pass through the opening.

2. The closure of claim 1, further comprising a sheet of bioresorbable material fixed to the first closure element adjacent or over the second narrowed end.

3. The closure of claim 2, wherein the sheet is fixed to an external portion of the first mesh enclosure.

4. The closure of claim 1, wherein each of the enlarged ends of the tether comprise a bead or a knot.

5. The closure of claim 1, further comprising a control wire looped through the second enlarged end of the tether.

6. The closure of claim 5, wherein the control wire passes through the fourth narrowed end.

7. The closure of claim 1, fitted within a delivery device.

8. The closure of claim 1, wherein the first and second narrowed ends are aligned with each other.

9. The closure of claim 1, wherein the third and fourth narrowed ends are aligned with each other.

10. The closure of claim 1, wherein the first and second narrowed ends are laterally offset with respect to each other.

11. The closure of claim 1, wherein one of the first and second narrowed ends is larger in diameter than the other of the first and second narrowed ends.

12. A device for closing an opening in the right atrial appendage of a patient, comprising:
a delivery device having a first peel-away catheter, a second tube within the first peel-away catheter, and a pusher tube within the second tube; and
the closure device of claim 1 fitted within the delivery device.

13. The device of claim 12, wherein the first closure element is within the first peel-away catheter and the second closure element is within the second tube.

14. The device of claim 12, further comprising a control line looped through the second enlarged end of the tether.

15. The device of claim 14, further comprising a control cannula extending through the pusher tube, and wherein the control line extends through the control cannula.

16. The device of claim 15, wherein the control line extends from the control cannula and returns to the control cannula from the second enlarged end of the tether, so that a free end of the control line is within the control cannula.

17. A method of closing an opening in the right atrial appendage of a patient, the method comprising:
advancing a placement device through a delivery sheath, the delivery sheath having a distal end positioned on a distal side of the opening, the placement device comprising an inner tubular member within an outer tubular member, and a closure device contained within said inner tubular member, the closure device comprising:
a first closure element, the first closure element having a first mesh enclosure, the first mesh enclosure having a first distal narrowed end and a second proximal narrowed end and a central volume, the first closure element contained within the outer tubular member;
a second closure element, the second closure element having a second mesh enclosure, the second mesh enclosure having a third distal narrowed end and a fourth proximal narrowed end and a central volume, the second closure element contained within the inner tubular member; and
a tether joining the first and second closure elements, in an initial configuration prior to delivery of the closure elements to the opening, the tether having first and second ends, wherein the first distal narrowed end of the first closure element is configured to anchor the first end of the tether and the second end of the tether is within the central volume of the second closure element;
removing the outer tubular member;
advancing the first closure element from the distal end of the delivery device;
withdrawing the delivery sheath through the opening while maintaining tension on the first closure element against the distal side of the opening;
advancing the second closure element from the distal end of the delivery device; and
securing the second delivery device against the proximal side of the opening.

18. The method of claim 17, wherein said securing comprises pulling a locking member positioned on the teacher through the fourth proximal narrowed end of the second closure element in a proximal direction, wherein the locking member is configured such that it cannot pass through the fourth proximal narrowed end in a distal direction.

19. The method of claim 17, wherein the outer tubular member comprises a peel-away catheter, and wherein said removing comprises peeling the outer tubular member from the inner tubular member.

20. The method of claim 17, wherein the delivery sheath is anchored at or near the distal side of the opening by a balloon member at or near the distal end of the delivery sheath.

* * * * *